(12) United States Patent
Gershater et al.

(10) Patent No.: US 10,590,494 B2
(45) Date of Patent: Mar. 17, 2020

(54) MULTIFACTORIAL PROCESS OPTIMISATION METHOD AND SYSTEM

(71) Applicant: SYNTHACE LIMITED, London (GB)

(72) Inventors: Markus Christian Gershater, London (GB); Sean Michael Ward, London (GB); Michael Ian Sadowski, London (GB); Christopher Richard Grant, London (GB)

(73) Assignee: Synthace Limited, London (GB)

( * ) Notice: Subject to any disclaimer, the term of this patent is extended or adjusted under 35 U.S.C. 154(b) by 389 days.

(21) Appl. No.: 15/270,837

(22) Filed: Sep. 20, 2016

(65) Prior Publication Data

US 2017/0016079 A1 Jan. 19, 2017

Related U.S. Application Data

(63) Continuation of application No. PCT/US2015/022275, filed on Mar. 24, 2015.

(30) Foreign Application Priority Data

Mar. 24, 2014 (GB) .................................. 1405243.5

(51) Int. Cl.
| | |
|---|---|
| *G01N 33/48* | (2006.01) |
| *C12Q 3/00* | (2006.01) |
| *G06F 16/2457* | (2019.01) |
| *G16B 5/00* | (2019.01) |

(Continued)

(52) U.S. Cl.
CPC ......... *C12Q 3/00* (2013.01); *G06F 16/24575* (2019.01); *G06F 16/24578* (2019.01); *G16B 5/00* (2019.02); *G16C 99/00* (2019.02)

(58) Field of Classification Search
None
See application file for complete search history.

(56) References Cited

FOREIGN PATENT DOCUMENTS

| WO | 2010/098865 A1 | 9/2010 |
| WO | 2012/045088 A9 | 7/2012 |

OTHER PUBLICATIONS

Boettner, et al., "High-throughput screening for expression of heterologous proteins in the yeast *Pichia pastoris*", Journal of Biotechnology, vol. 99, Issue 1, Oct. 9, 2002, pp. 51-62.

(Continued)

*Primary Examiner* — Eric S Dejong
(74) *Attorney, Agent, or Firm* — Perkins Coie LLP; Viola T. Kung

(57) ABSTRACT

A method and system for increasing process performance in a biological process comprising at least one process step, the method comprising: (a) an identification phase, in which at least seven factors are identified, wherein a factor is defined as a feature of or within a process that when modified will affect the performance of the process, and wherein the factors are selected from at least one process factor and at least one genetic factor; (b) a factor screening phase, in which individual and combined contributions to process performance of each of the at least seven factors are determined, such that at least one multi-factorial interaction is identified; and (c) a refinement phase, in which higher order interactions that result in an increase in process performance between the at least seven factors are identified and tested. The method may be incorporated within automated laboratory and design of experiment systems.

14 Claims, 12 Drawing Sheets

(51) Int. Cl.
*G16C 99/00* (2019.01)
*G06G 7/58* (2006.01)

(56) References Cited

OTHER PUBLICATIONS

Davidson, et al., "Building Synthetic Systems to Learn Nature's Design Principles", Advances in Experimental Medicine and Biology, vol. 751, Jun. 9, 2012, pp. 411-429.

Fu, Zhibiao et al., "Optimization of a *Saccharomyces cerevisiae* fermentation process for production of a therapeutic recombinant protein using a multivariate bayesian approach", Biotechnology Progress., vol. 28, No. 4, Jun. 18, 2012 (Jun. 18, 2012), pp. 1095-1105.

Isalan, et al., "Evolvability and hierarchy in rewired bacterial gene networks", Nature, vol. 452, Apr. 17, 2008, pp. 840-846.

Lu, et al., "Shuffling of Promoters for Multiple Genes to Optimize Xylose Fermentation in an Engineered *Saccharomyces cerevisiae* Strain", Applied and Environmental Microbiology, vol. 73, No. 19, Oct. 2007, pp. 6072-6077.

Orban, E. , "Effect of temperature and yeast concentration on the autolysis of Kluyverommyces fragilis grown on lactose-based media", Journal of Food Engineering, vol. 21, No. 2, Jan. 1, 1994 (Jan. 1, 1994), pp. 245-261.

Saxena, Deepali et al., "Process optimization for a nutritious low-calorie high-fiber whey-based ready-to-serve watermelon beverage", Journal of Food Science and Technology, Springer (India) Private LTD, India, vol. 52, No. 2, Jun. 25, 2013 (Jun. 25, 2013), pp. 960-996.

Weuster-Botz, , "Experimental Design for Fermentation Media Development: Statistical Design or Global Random Search?", Article in Journal of Bioscience and Bioengineering vol. 90, No. 5, n Nov. 2000, pp. 473-483.

International Search Report dated May 29, 2015 in PCT Application No. PCT/US2015/022275.

Supplementary European Search Report dated Sep. 11, 2017 in EP Application No. 15769236.9.

MULTIFACTORIAL PROCESS OPTIMISATION METHOD AND SYSTEM

This application is a continuation of PCT/US2015/022275, filed Mar. 24, 2015, which claim priority to GB 1405243.5, filed Mar. 24, 2014. The contents of the above-identified applications are incorporated herein by reference in their entirety.

FIELD OF THE INVENTION

Methods and systems for design and execution of experiments are considered in this invention, in particular design and implementation of complex optimizations of bioprocess manufacturing or laboratory protocols.

BACKGROUND OF THE INVENTION

There are very large numbers of variables that influence the overall yield of product in a biological synthetic process, for example the host organism selected, the genetic modifications of the host and physical factors such as medium composition, temperature, pH and oxygen availability. The question of how to design the most efficient process given the influence of so many variable factors is therefore one of searching a very high dimensional space for areas of maximal reproducible yield of the required output such as a product. A common approach in the art is to optimise one factor at a time—the combinatorial increase in complexity of investigating increasing numbers of factors simultaneously is seemingly an insurmountable barrier to many researchers. Although this approach has the appeal of conceptual simplicity and may be taught as good experimental practice it is a highly inefficient bioprocess optimization strategy since biological systems are inherently multi-factorial in nature. Consequently, manufacturing processes that require the use of live organisms, enzymes or cellular extracts developed using the one factor at a time approach frequently suffer from issues such as unacceptable levels of batch-to-batch variability, poor product yields or both. These characteristics are not suitable for quality manufacturing processes and represent a considerable barrier to those wishing to utilise bioprocessing steps in manufacturing systems.

Despite these problems many successful bioprocesses have been developed and there is a recognised potential for bio-based manufacturing to provide enormous benefits across many areas. To overcome this problem requires the adoption of multifactorial methods to identify key sources of process variability and identify higher process yields, thereby substantially de-risking bioprocess development. To achieve this, there exists a need in the art to provide methods and systems that can facilitate reliable design of experiments from the level of the lab bench up to and including the industrial-scale bioreactor. These and other uses, features and advantages of the invention should be apparent to those skilled in the art from the teachings provided herein.

SUMMARY OF THE INVENTION

In accordance with the present invention, a first aspect provides a method for increasing process performance in a biological process comprising at least one process step, the method comprising:
(a) an identification phase, in which at least seven factors are identified, wherein a factor is defined as a feature of or within a process that when modified will affect the performance of the process, and wherein the factors are selected from at least two process factors and at least two genetic factors;
(b) a factor screening phase, in which individual and combined contributions to process performance of each of the at least seven factors as described in (a) are determined, such that the presence of multifactorial interactions might be identified; and
(c) a refinement phase, in which interactions that result in an increase in process performance between the at least seven factors are identified and tested.

Typically, the biological process comprises a plurality of process steps, wherein the at least one process step comprises a manufacturing process, and/or suitably the at least one process step comprises an analytical process.

In a specific embodiment, each factor is modified over at least two levels, wherein a level corresponds to a parameter range or characteristic associated with the factor. Suitably, the multi-factorial interaction comprises at least one two-factor interaction, optionally at least one three-factor interaction, specifically the multi-factorial interaction may comprise at least one interaction that comprises more than three factors. In a particular embodiment of the invention, the multi-factorial interaction comprises at least one process factor and at least one genetic factor.

In a further embodiment of the invention the at least one process factor is selected from the group consisting of: temperature; pH; titrants; buffer concentration; reagent concentration; growth media composition; nutrient concentration; waste-product concentration; oxygen concentration; reactor volume; fermentation volume; impeller speed; seed culture conditions; air flow; pressure; feed composition; feed rate; feed timing; antifoam type; antifoam concentration; shaking speed; presence of baffles; size of baffles; position of baffles; bioreactor geometry; inducer concentration; induction time; stock culture generation method; stock culture storage conditions; and timings of any process step.

In yet a further embodiment of the invention. the at least one genetic factor is selected from the group consisting of: vector type; genetic background; epigenetic modifications; gene variant; gene identity; host organism species; host organism strain; promoter type; codon usage; ribosome binging site; origin of replication; selection marker; site of chromosomal integration; leader sequence; fusion protein; fusion tag; siting of fusion element at N or C terminus; operator usage; activator usage; operon design; mRNA 5' optimisation strategy; copy number; orientation of genetic constructs; insulator elements; siRNA candidates; non-coding nucleic acid; gene knockouts; and gene upregulation.

Optionally, the method may comprises at least one further step:
(d) an optimisation phase, in which higher order interactions are used to generate a higher-order model based upon a limited number of factors identified as contributing most significantly to an increase in process performance.

A second aspect of the invention provides a computer implemented method comprising any of aforementioned methods described herein.

A third aspect of the invention provides a system for increasing process performance in a biological process, the system comprising:
(i) a processor adapted to implement any of the methods as described herein; and (ii) a laboratory automation apparatus, wherein the apparatus is controlled by the processor and is configured so as to implement the factor screening and refinement phases.

Optionally, the laboratory automation apparatus is further configured so as to implement the optimisation phase. In embodiments of the invention the laboratory automation apparatus comprises one or more of the group consisting of: liquid handling and dispensing apparatus; container handling apparatus; a laboratory robot; an incubator; plate handling apparatus; a spectrophotometer; chromatography apparatus; a mass spectrometer; thermal-cycling apparatus; and centrifuge apparatus. Suitably, the processor implements the method of the invention as part of a laboratory information management system (LIMS).

DETAILED DESCRIPTION OF THE INVENTION

Figure 1:
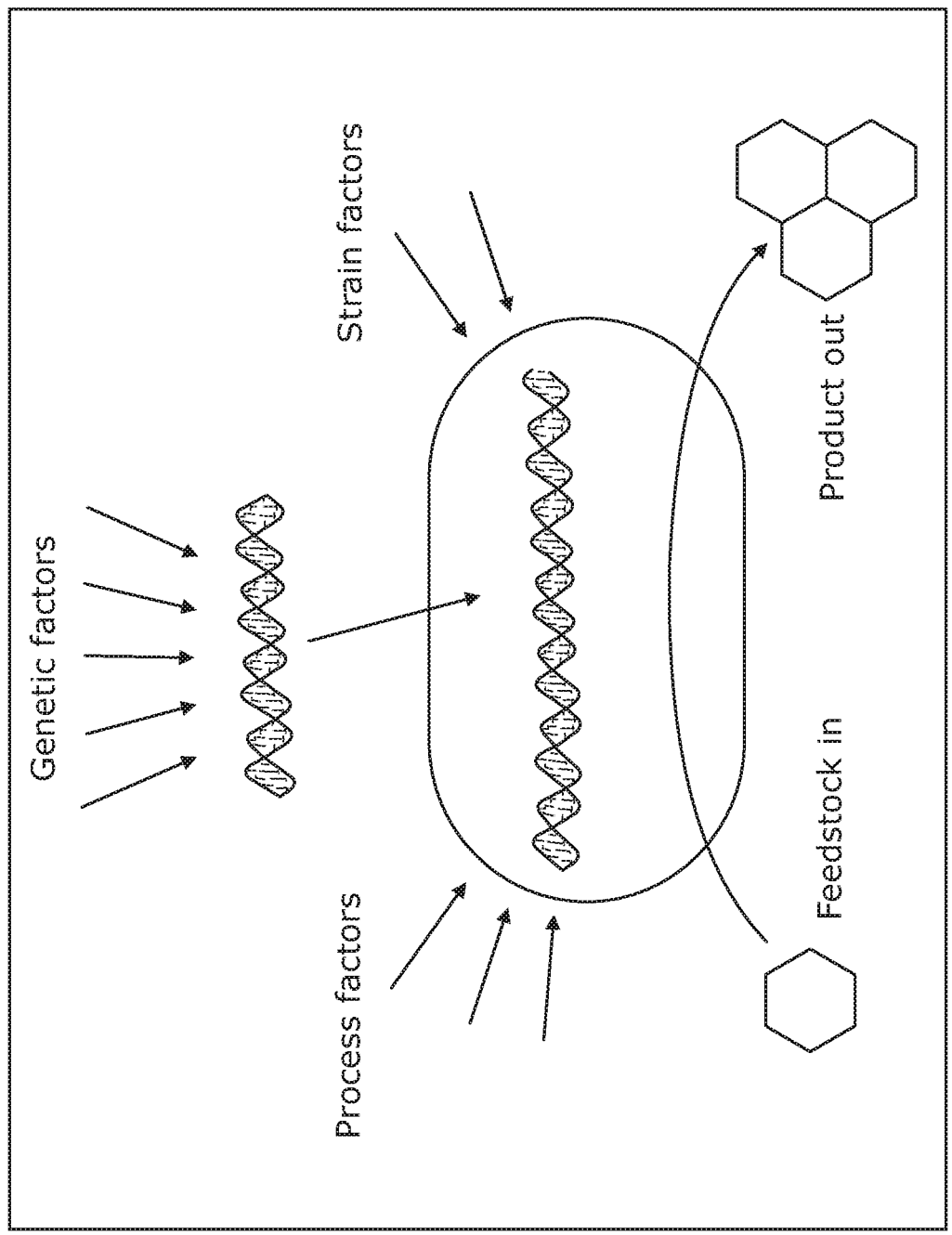
FIG. 1 is a schematic representation of typical factors that may influence the success of a notional bioprocess.

All references cited herein are incorporated by reference in their entirety. Unless otherwise defined, all technical and scientific terms used herein have the same meaning as commonly understood by one of ordinary skill in the art to which this invention belongs.

Prior to setting forth the invention, a number of definitions are provided that will assist in the understanding of the invention.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

The term "process" is defined as a specific sequence of transformative events performed upon a starting material in order to achieve a specified purpose or goal. The process may result in the transformation of the starting material into a product—in which case the process is a "production process". Alternatively, the process may result in the determination of information about the starting material—in which case the process may be diagnostic or prognostic in nature. The overall process may be sub-divided into individual process steps that are applied in sequence to achieve the desired outcome. According to an embodiment of the invention, the process is a "bio-process" that uses complete living cells or their components (e.g., prokaryotic or eukaryotic cells, enzymes, organelles such as chloroplasts) to obtain desired products. The processes of the present invention are subject to process variables that are referred to as factors. Hence, a process comprises a set of steps that are applied on inputs (including at least a physical input) in order to produce an output (including at least a physical output such as a product, and possibly additional data outputs). An embodiment of the invention may include a process which involves the introduction of one or more genes into a microorganism, which in turn expresses one or more proteins encoded by those genes or modifies the metabolic processes of the organism by the expression of non-protein-coding genes or other alterations to the genetic makeup of the host. The protein(s) itself is may be the desired product or where it functions as part of a pathway, the protein may contribute to the generation of a desired product.

The term "product" is defined as any desirable physical output of a process. Suitably, a product may include an eukaryotic or prokaryotic organism, virus, nanostructure, protein, polypeptide, polynucleotide, polymer, complex or small molecule that is produced as a result of the process. It will be appreciated that the aforementioned does not represent an exhaustive list of potential products, which are typically reliant upon the precise nature of the process that is to be undertaken.

The term "factor" is used herein to denote any defined feature of or within a process that can be modified without changing the ultimate goal of the process. According to one embodiment of the present invention there are two categories of factors: genetic and process factors.

"Process factors" suitably relate to features of a process which are not associated with the genetics of a construct or host. Typical process factors may include features of the equipment (e.g. dimensions of a reaction tank, impeller configurations, siting of probes), environment (e.g. temperature, pH, oxygenation), protocol (e.g. timings of significant stages and events such as inoculation and induction), reagents (growth media composition, nutrient level, feedstock concentration, inducer concentration), handling of cells (stock storage conditions, size of inoculations between reactors), process design (number of process steps, type of reaction vessel). It will be appreciated that the aforementioned does not represent an exhaustive list of potential process factors, which are typically reliant upon the precise nature of the process that is to be undertaken.

"Genetic factors" suitably relate to qualitative and quantitative features associated with any genetic material involved in a process, for example, such as features of the specific genetic 'construct' which is used to introduce new nucleic acid, including DNA, into the host (e.g. identity or composition of vector), features of the host microorganism (e.g. strain, genetic background (including knockouts of undesirable genes) and protein overexpression, epigenetic factors), features of functional DNA (e.g. gene identity, promoter strength, ribosome binding site strength, plasmid origin of replication, terminator, codon usage strategy, operator, activator, gene variant). In an instance where a bioprocess involves whole genomic interaction, it will be appreciated that each gene, non-coding genetic element and epigenetic modification could be considered as an individual genetic factor, leading to a complexity involving hundreds or even thousands of factors. It will be appreciated that the aforementioned does not represent an exhaustive list of potential genetic factors, which are typically reliant upon the precise nature of the process that is to be undertaken.

Factors, whether process or genetic factors, are deemed to interact when the effects of changes to one factor are dependent on the value of another factor. Typically, a given process step within a process—such as a bioprocess—may comprise a plurality of factors that can interact with each other. Hence, when one factor is altered as a result of a change in a process parameter, or the inherent characteristics associated with that factor are changed, there can be a cascade of interactions that will modify the effects of other factors within that process step in a causative manner. Where a process comprises more than one process step, this cascade of interactions may lead to additional interactions within factors of neighbouring or even distant process steps. It follows, therefore, that many processes can be considered to be multi-factorial in nature.

According to the present invention, the term "multi-factorial" when applied to a given process refers to a situation where multiple known factors are considered to be likely to influence the output (e.g. quantity, quality or identity of products) or characteristics (e.g. time, cost, infrastructure requirements) of the process. Typically a multi-factorial interaction comprises at least one two-factor interaction, optionally at least one three-factor interaction. In some instances, the multi-factorial interactions observed may comprise a plurality of two-factor and/or three-factor (or more) interactions.

In an embodiment of the present invention, a process or process step is considered where at least seven individual factors are identified as potentially relevant to the performance of the process or process step, leading to the identification of at least one multi-factorial interaction. Suitably the at least seven factors may be selected from: all process factors; all genetic factors; or a combination of process and genetic factors. In a specific embodiment of the invention the number of factors required for consideration is greater than 8; greater than 9; greater than 10; greater than 11; greater than 12; greater than 13; greater than 14, and optionally at least 15. In a specific embodiment of the invention the number of factors required for consideration may be up to or in excess of 500, 1000 or even 100,000.

It is usual that when a given process involves at least one step or sub-step that requires involvement of a biological organism then at least two genetic factors will be considered within the multi-factorial process of the invention. Depending upon the total number of factors to be considered, if the process requires use of a biological organism or an extract from a biological organism, then at least 10% of the total number of factors selected should comprise genetic factors. Optionally, the number of genetic factors as a proportion of the total may be at least around 20%, alternatively at least around 40%, and suitably up to around 70%, specifically up to at least around 90% of the total number of factors. In a particular embodiment of the invention the process is a bio-process in which number of factors is at least seven, where at least two are selected from genetic factors.

The invention provides a novel methodology that uses the combination of fractional factorial design of experiments, factor screening and filtering in order to derive a highly efficient methodology for improving the process. A specific embodiment of the invention works by building a series of multidimensional linear models from experimental data and approximating the response surface as a function of the experimental factors. The required number of experiments at each stage is kept feasible by constraining the objectives of each iteration of the process. The iterative nature of the process allows migration over the response surface to an optimal region. For the search process to find an optimum it requires the input of significant domain expertise at each stage. If at any point the domain expertise is considered limiting, the experiments can be expanded to accommodate uncertainties.

Figure 2:
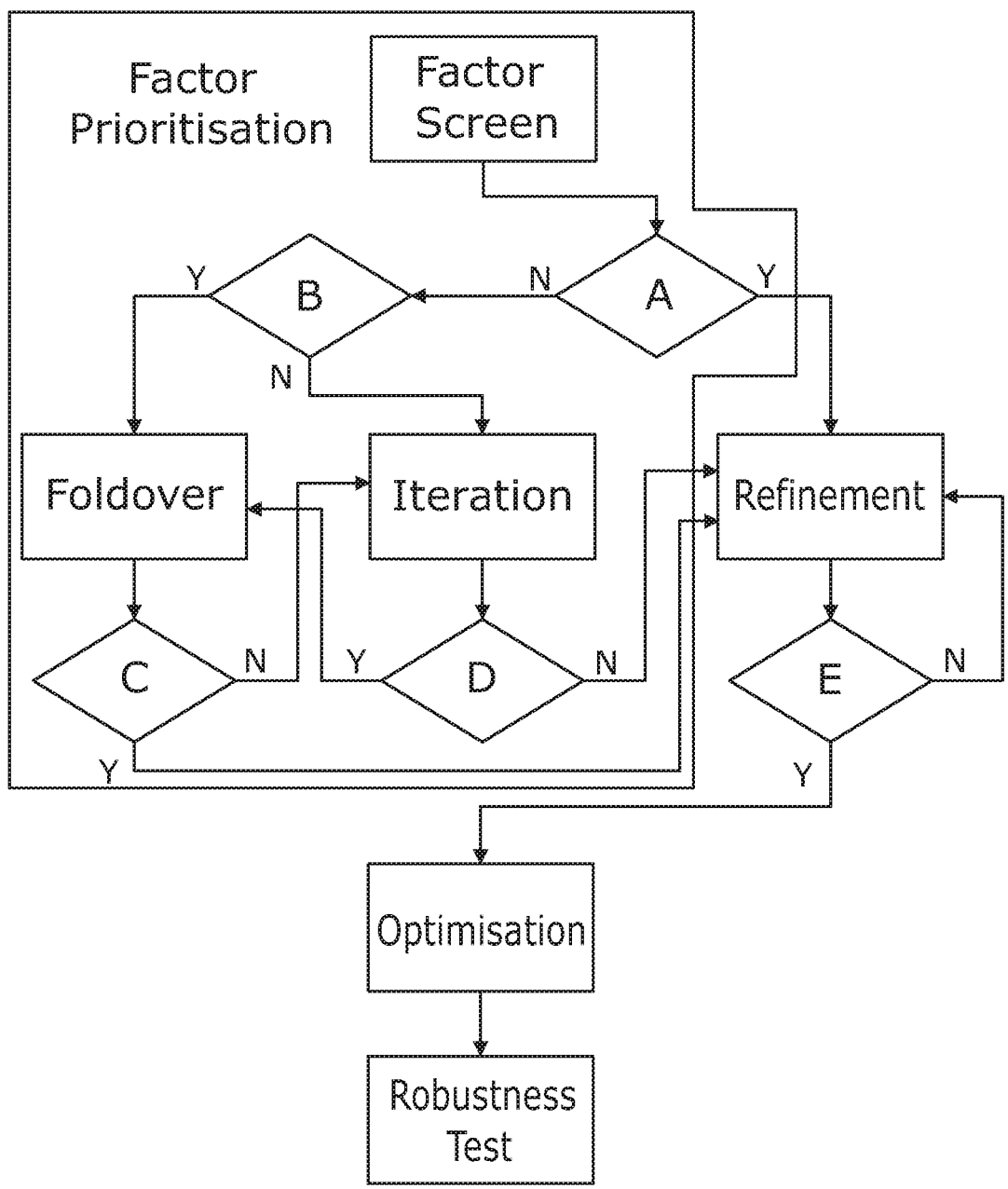
FIG. 2 is a flowchart of iterative experimental strategy according to one embodiment of the invention.

FIG. 2 shows a flow chart of a process according to an embodiment of the present invention. At the factor mining step, a user may specify factors (genetic and/or process factors) to test and levels to test them at, optionally either factors, levels or both may be defined by an automated process which may for example be the result of machine learning trained on some combination of prior experimental data and externally derived information. Then, at the factor prioritisation step, experimental data are used to define the factors of most importance for more in-depth investigation. A preliminary model of the response surface is fitted using $1^{st}$ order polynomials containing single factors and multi-factor interactions. The aim is to do sufficient experimentation to be able to choose the most important factors from the original list. This can involve iterations of the original design to move the design space to a more productive and information dense area, and fold-overs, which are a way of defining multifactor interactions. At the refinement step, a more focused investigation of the factors of most importance is performed, with the aim of defining more multifactor interactions. The optimisation step comprises augmented designs focussing on a still-smaller subset of the most critical factors, aiming to model using $2^{nd}$-order polynomials. Finally, robustness tests are performed, in which experiments around a predicted optimum are performed to test the model and investigate the robustness of the process. Each of these steps is described in detail below.

The factor mining step requires the definition of which factors will be varied in the process or sub-process under consideration and which initial levels are to be chosen. Since the overall process is effectively a local search by gradient ascent, the initial screen essentially determines the size of the final optimum. This, therefore, relies to an extent on some prior knowledge available for the bio-based manufacture of the desired product; or where the process is analytical in nature for the analysis of the starting material. Existence of prior knowledge is not essential for performance of the invention as this can be mitigated by using the initial screening trials to identify a suitable starting point. The factors that are typically identified for screening include two principal categories: process factors and genetic factors.

The screening step aims to find the experimental factors leading to high product yield and eliminate unimportant factors. The screening stage uses a fractional factorial strategy. This attempts to estimate coefficients of a linear model in n factors. The model is a first-order polynomial in which the terms are all single factors ("main effects", e.g. A, B, C) and low-order interactions between the factors (e.g. AB, AC, ABC). This allows detection of the effects of individual factors, such as temperature or pH, as well as synergistic effects such as those which only occur at high temperature and low pH, for example.

To assess the contribution of variation of a factor to the measured outputs of a process or sub-process it is sufficient in most cases to assign the settings of that factor to be at either of two levels in any particular experimental run. Comparison of outputs for all runs at each of the two levels by averaging allows an estimation to be made of the gradient of the multidimensional response function local to the centre of the design space in question. Interaction terms can be identified as differences in observed gradient for a particular factor given settings of other factors from those expected based on the gradient calculated for any contributing factor singly.

Simultaneous estimation of these gradients allows construction of a mathematical model approximating the surface of the response function local to the process settings in question which can be used as a basis for further optimisation. Experimental efficiency in the face of factorial complexity in the number of potential interactions as a function of the number of factors can be maintained by use of the limiting assumption that the majority of these interactions will make a very small contribution to the overall variability in process performance and therefore the number of gradients of interest is a relatively small subset of the very large number possible.

By way of example, in a process that has three factors denoted as factors A, B and C and where each factor is varied at two possible levels, the set of effects to be estimated contains all single factors (A, B, C) and all interactions (AB, AC, BC, ABC), 7 in total. Expressed as a linear model this could be written:

$$Y=\beta_0+\beta_1 A+\beta_2 B+\beta_3 C+\beta_4 AB+\beta_5 AC+\beta_6 BC+\beta_7 ABC$$

Coefficient $\beta_0$ models the intercept, $\beta_{1-3}$ the strengths of the main effects, $\beta_{4-6}$ two factor interactions (2FIs) and $\beta_7$ the single three factor interaction (3FI).

In this example, eight experiments ($2^3$) in which the levels of each of the three factors are varied over two levels (+1 or −1) to cover all eight possible combinations would have to be performed. By performing $2^n$ experiments one is able to estimate $2^n$ model terms although in practice it is necessary to sacrifice at least one experiment for the estimation of model error, allowing $2^n-1$ terms to be estimated. This would be tolerable in this exemplary case; however the exponential dependence of the total number of model terms on the number of factors renders this strategy prohibitive for use in instances where greater numbers of factors, in the tens or hundreds, need to be considered.

By utilising the method of fractionating the experimental design to estimate a subset of model terms, preferentially assigning runs to low-order interactions at the expense of high-order interactions, an embodiment of the present invention provides an improved method in order to determine which experiments should be performed so as to identify the most relevant factors and interactions required to optimise any given process.

One issue when exploring larger numbers of factors is to notice that as the number of factors increases the majority of experiments contribute to estimating the coefficients of medium to high order interactions between factors. One can therefore improve efficiency if there is a reason that these model terms are unlikely to be significant. At the screening stage the set of factors inevitably contains some which do not affect the response and interactions with these are highly likely to be insignificant. Significant interactions containing more than three factors are also generally observed to be rare and low in magnitude. On this basis the number of runs can be reduced by removing experiments which contrast between high-order interaction terms while ensuring that appropriate contrasts remain to distinguish between main effects and low-order interactions. This is known as a fractional factorial design.

The method of fractional factorial designs in detail may be undertaken as follows: since the design requires $2^n-1$ coefficients to be estimated using $2^{n-k}$ vectors it follows that some terms must have the same pattern of contrasts as others, therefore becoming indistinguishable (aliased). Specifying an adequate design requires assigning factors appropriately so that these aliased model terms are sets containing at most one low-order term. Judicious selection of aliasing patterns is also key to correctly specifying the design: an assignation of factors should be undertaken such that aliased interactions generally have at most one plausible interaction in any set. Where the experiments find a significant term which has several plausible explanations as a result of aliasing a minimal extension to the design is made to provide the additional runs required to determine which of the candidates is actually contributing to the measured effect. This is referred to as a foldover procedure. Selection of aliasing may be undertaken by manual or automated means, including artificial intelligence (AI) algorithms.

Factorial designs may be analysed by a standard analysis of variants (ANOVA) method. Optionally, transformation of the response variable using the power transformation found by the procedure of Box & Cox may be performed beforehand (Box & Cox (1964) J. Royal Stat. Soc. B 26:211-252). Effect sizes for main effects and interactions are found as the difference between average response values for the high (+1) and low (−1) levels. The first-order model may be specified by a manual or automated choice of significant terms by reference to a half-normal plot. The adequacy of the full model and each contributing term is then assessed by partitioning the sum-of-squares contributions to the variance and assessing significance using the F distribution.

Additional diagnostic methods may be performed to ensure the method is robust to outliers: residuals may be plotted against run order and effect sizes to screen for outliers and test adequacy of model assumptions. The procedure of Box & Cox may also be useful in identifying dependence of variance on response sizes. A normal probability plot of residuals can be used as a further test of model adequacy in addition to the Shapiro-Wilk test to assess deviations from normality in the distribution of error terms (Shapiro & Wilk (1965) Biometrika 52 (3-4): 591-611).

Screening typically takes place over several iterations aiming to locate a region with high values and suitably low levels of variation of the required responses. Using gradient information obtained from the first-order model the surface is navigated using an optimization process, including but not limited to gradient ascent, conjugate gradient methods, Newton-Raphson optimization, rank-one, rank-two and the Newton-Lagrange algorithm, until a suitable threshold value is achieved or other termination criteria (e.g. resource limits or the limit of feasible factor settings) are met. Following this the need for further optimisation is assessed using the lack-of-fit value for the resulting model and economic considerations. The output of the screening step is a parameterised first order polynomial model. This allows one to establish which factors are contributing to the variability of responses, approximate levels at which they should be set and determine which factors can be eliminated.

In the refinement step, a moderately extended design including 3 levels per factor (with replication over categoric factors) may be implemented to acquire better parameter estimates and determine the need for adopting a more complex model. This can be performed by comparison between the model value prediction for the centrepoint and its measured value. Incorporation of this into the ANOVA procedure allows the contribution of curvature in the response surface to the overall variance to be assessed.

The optimisation step typically uses a response surface methodology (RSM) to fit a higher-order model (typically quadratic) in a small number of factors based on the last-stage factorial experiment, however the invention should be understood to include other optimization methods including but not restricted to: Newton-Raphson, Newton-Lagrange, rank-one, rank-two, steepest ascent, conjugate gradient and support vector machine regression. The most appropriate extensions depend on the details of the model to be fitted and expectations of the geometry of the space. For example, a central composite design may be used, in which the number of factor levels is increased from three to five and a quadratic model is estimated. Values for the additional levels are chosen as the two factorial levels±α and the centrepoint. The design should be replicated for each combination of categorical factors. The value of α is preferably chosen to permit rotation of the resulting model where constraints on factor levels do not prevent this.

A crucial question addressed by these methods is that of model selection between linear, quadratic and higher-order models. The structure of the experiment is critical in ensuring estimability of a model of correct order: the Box-Wilson central composite design, for instance, restricts models to order 2 or lower. Estimation of more complex model forms including non-linear models may be performed using applicable experimental designs derived via optimal design methods or machine-learning based "active learning" approaches. Additionally it is necessary to add extra runs to estimate experimental error and to permit lack-of-fit testing by cross-validation. In this process additional experimental runs which are excluded from the set used to derive model parameter estimates are performed; these runs may be chosen to be replicates of runs already in the design, other points within the design space or external to it to permit tests of both interpolation and extrapolation to be performed. Models may for example be optimised using automated stepwise regression with manual intervention where necessary, or via standard processes of nonlinear optimization or by application of machine learning methods including but not restricted to support vector machines, artificial neural networks and metaheuristic methods. The resulting model can be used to define experimental conditions for production. Optional confirmatory runs can be used to determine the degree of agreement between predicted and actual values.

Statistical tools for generating and analysing experimental designs according to the methodology of the present invention are available and may include packages such as Design-Expert® (Stat-Ease, Inc., Minneapolis, Minn., USA).

In a specific embodiment of the invention, the described method can be implemented via one or more computer systems. In another embodiment the invention provides a computer readable medium containing program instructions for implementing the method of the invention, wherein execution of the program instructions by one or more processors of a computer system causes the one or more processors to carry out the phases as described herein. Suitably, the computer system includes at least: an input device, an output device, a storage medium, and a microprocessor). Possible input devices include a keyboard, a computer mouse, a touch screen, and the like. Output devices computer monitor, a liquid-crystal display (LCD), light emitting diode (LED) computer monitor, virtual reality (VR) headset and the like. In addition, information can be output to a user, a user interface device, a computer-readable storage medium, or another local or networked computer. Storage media include various types of memory such as a hard disk, RAM, flash memory, and other magnetic, optical, physical, or electronic memory devices. The microprocessor is any typical computer microprocessor for performing calculations and directing other functions for performing input, output, calculation, and display of data. Two or more computer systems may be linked using wired or wireless means and may communicate with one another or with other computer systems directly and/or using a publicly-available networking system such as the Internet. Networking of computers permits various aspects of the invention to be carried out, stored in, and shared amongst one or more computer systems locally and at remote sites. In one embodiment of the invention, the computer processor may comprise an artificial neural network (ANN). In a further embodiment of the invention the method may be incorporated as part of a laboratory information management system (LIMS) or a software suite that is compatible with a LIMS.

The methods of the invention may be configured to interact with and control automated laboratory equipment including liquid handling and dispensing apparatus or more advanced laboratory robotic systems. Where higher numbers of factors are considered during the factor screening phase, in one embodiment of the invention it is an option to automate performance of factor screening experiments using a high-level programming language to produce reproducible and scalable workflows to underpin the screening, refining and optimisation phases of the method. Suitable high-level programming languages may include C++, Java™, Visual Basic, Ruby and PHP, as well as the biology specific language Antha™ (www.antha-lang.org).

The invention is further illustrated by the following non-limiting examples.

EXAMPLE

Example 1—Multi-Factorial Screen for a Bio-Process

Complex eukaryotic proteins, such as those of human origin, can present problems when produced in prokaryotic hosts such as *E. coli*. The target human enzyme carboxylesterase 1 (uniprot accession P23141) is no exception: prior art in the literature did show expression, but yields were poor (C. L. Morton, P. M. Potter: Comparison of *Escherichia coli, Saccharomyces cerevisiae, Pichia pastoris, Spodoptera frugiperda*, and COS7 cells for recombinant gene expression: application to a rabbit liver carboxylesterase. Mol.

Figure 3:
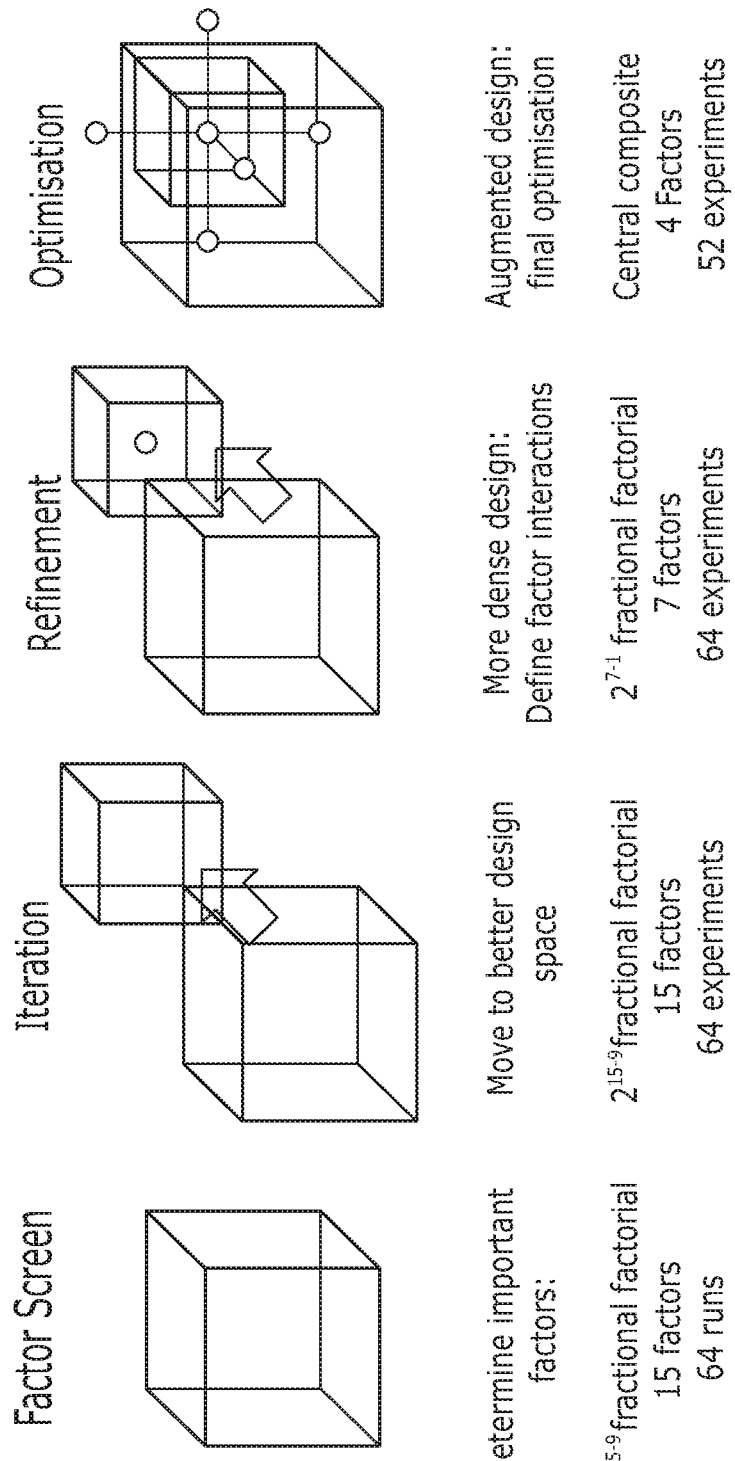
FIG. 3 is a diagrammatic representation of the stages employed to optimise enzyme production according to one embodiment of the present invention.

Biotechnol., 16 (2000), pp. 193-202). The main experimental steps of the process are summarised in FIG. 3.

Factor Mining

A full literature review and analysis of online databases was undertaken. When combined with in-house expertise this enabled the selection of 15 prioritised factors for investigation, and assignment of levels for each of those factors. Preliminary factor levels were set with the aim that if a particular factor could have an effect then the effect it would generate would be as large as possible within known constraints, to ensure it could be observed above experimental noise. An example is temperature: above 37° C. will usually be too high for E. coli, whilst it is known that eukaryotic (in this case human) proteins can often express better at lower temperatures. Literature precedent confirmed this, so 20° C. (level '−1') and 30° C. (level '1') was investigated. Twelve diverse process factors were included and three genetic factors pertaining to how the desired gene and related sequences were coded (e.g. ribosome binding site strength).

TABLE 1

Selected process and genetic factors for factor screen step of the multi-factorial analysis

| | Factor | Unit | −1 | 1 | Type |
|---|---|---|---|---|---|
| A | [Glucose] | g/L | 0 | 2 | Process |
| B | Overnight Growth Media | — | LB | TB | Process |
| C | [L-rhamnose] | mM | 0.1 | 2 | Process |
| D | Pre-Induction Time | hours | 2 | 4 | Process |
| E | Harvesting Time | hours | 8 | 24 | Process |
| F | Post-induction Temp | ° C. | 20 | 30 | Process |
| G | GroES/GroEL coexpression | — | no | yes | Genetic |
| H | Ribosome-Binding Site | — | ML | MH | Genetic |
| J | Plasmid Copy Number | — | Med | High | Genetic |
| K | Overnight Growth Temp | ° C. | 30 | 37 | Process |
| L | [Peptone] | g/L | 10 | 20 | Process |
| M | [Yeast extract] | g/L | 5 | 24 | Process |
| N | [Glycerol] | g/L | 0 | 5 | Process |
| O | [MgSO4] | g/L | 0 | 0.5 | Process |
| P | [NaCl] | g/L | 0 | 10 | Process |

Factor Screen

Figure 4:
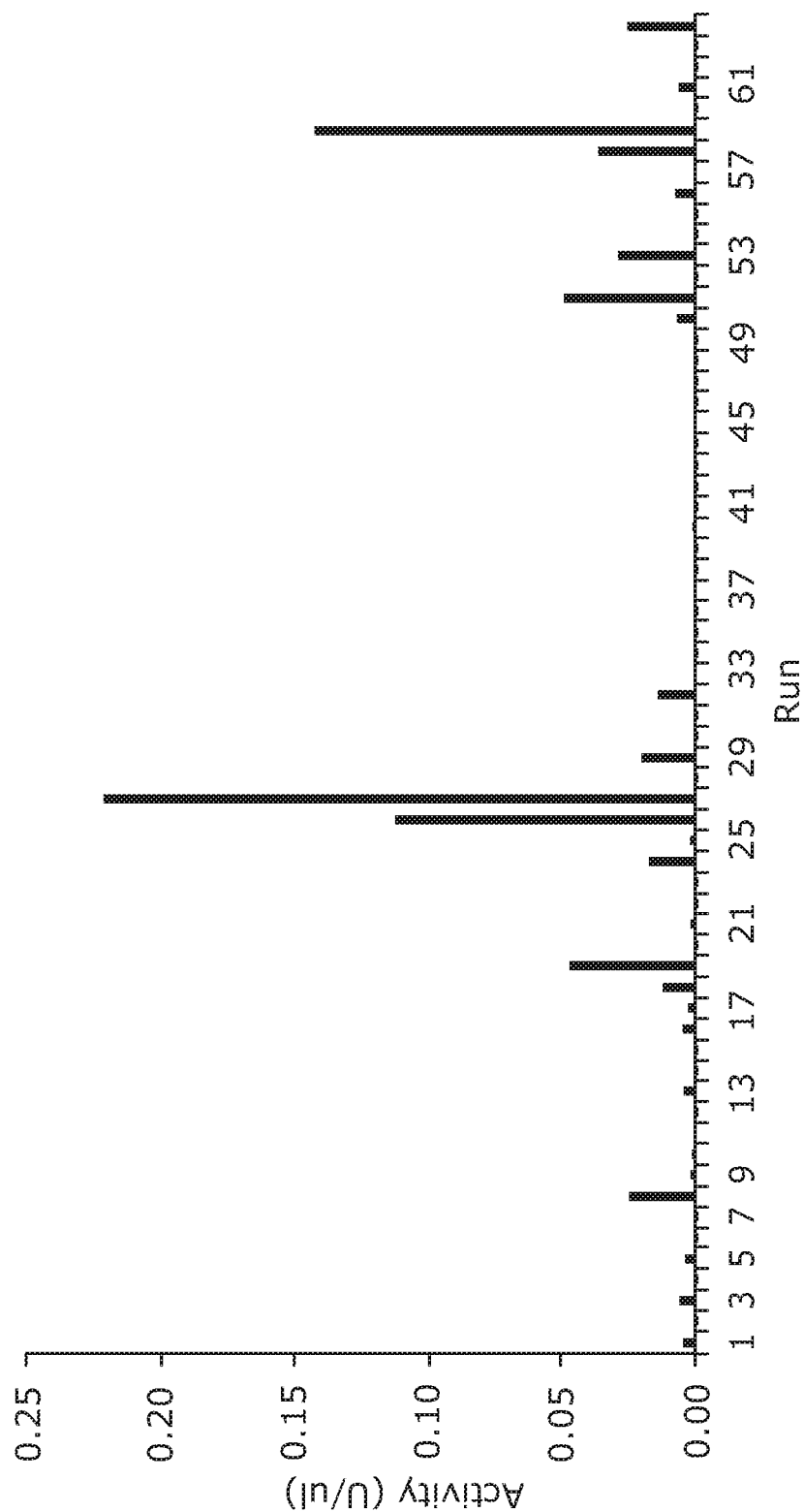
FIG. 4 is a graph of enzymatic activity observed per microliter of unpurified E. coli lysate from an initial factor screening step according to an embodiment of the invention.

Although the factor mining process highlights factors assessed as possibly being important, the complexity and unpredictability of biological systems dictates that screening is required to definitively determine which are having an effect on the process under optimisation. To screen the 15 selected factors, a $2^{15-9}$ fractional factorial was carried out: a design that made sure that all main effects were only aliased with three factor interactions (3FIs), whereas two factor interactions (2FIs) were aliased with other 2FIs and with 3FIs. This would allow identifying factors that had large influences on the response by themselves (main effects), while also identifying the presence of two factor interactions, although these would be in the form of lists of possible 2FIs as opposed to being fully defined. This is provided that any 3FIs would be rare and small in magnitude, an assumption made at this stage in the design of experiments strategy. Having obtained a design, the experiment was run, with the 64 specified runs giving responses as shown in FIG. 4.

Many zero responses were observed, however, there were sufficient data to observe the primary effects in the design that significantly influenced the responses. A half-normal plot was used to distinguish significant effects from those that are likely to be due to noise. Standardised effect sizes were plotted such that the lower magnitude effects are plotted more densely with respect to the y axis than those of greater magnitude, with the scale being determined by a half-normal distribution. Therefore, if the noise is normally distributed, insignificant factors should all be in a straight line, whereas significant factors should be to the right of this line.

Figure 5:
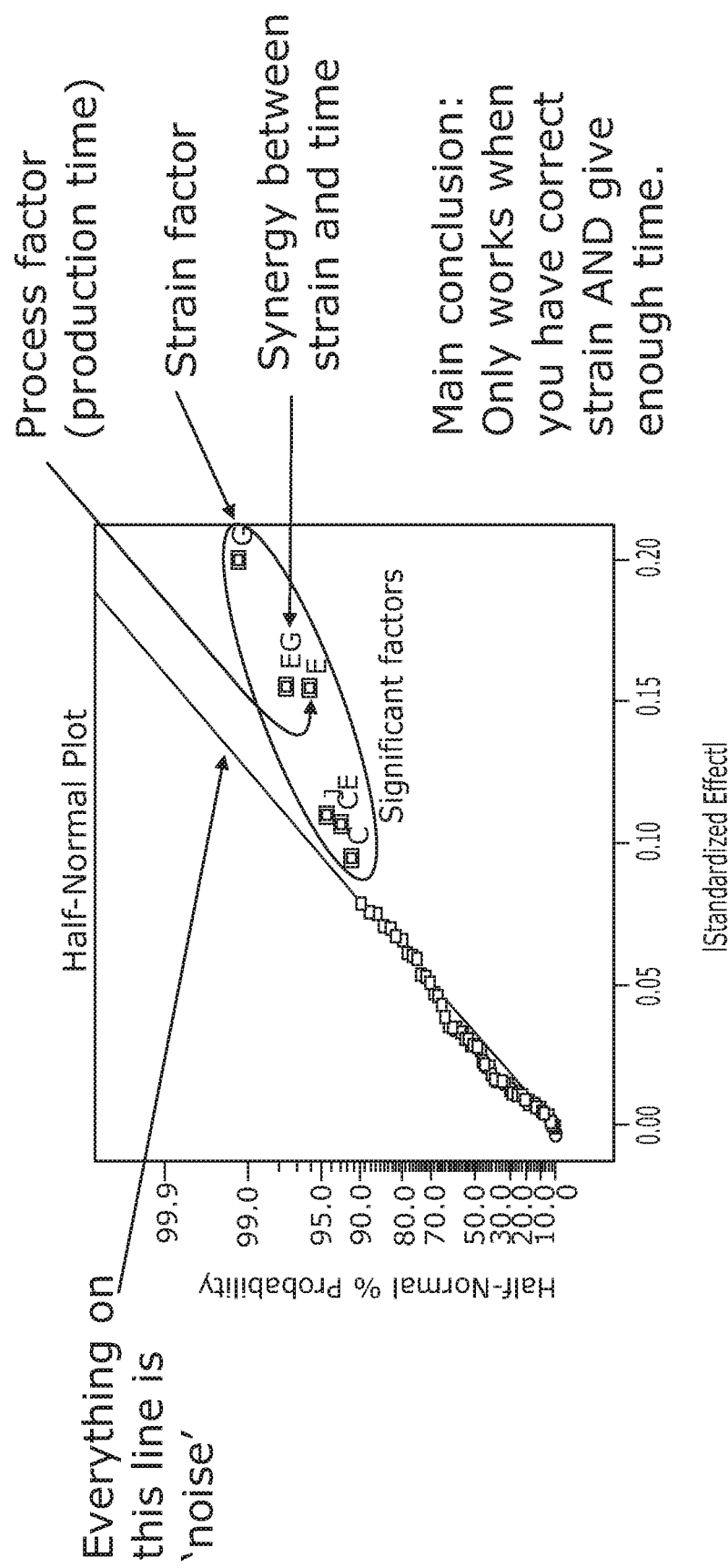
FIG. 5 is a half normal plot of the results obtained in the initial factor screen.

The largest effects displayed by the half-normal plot showed unexpectedly that the strain factor (G) was critical for target enzyme production, along with the amount of time allowed for the protein expression (E). Critically, there was also a large positive multifactor interaction indicated, that was a sum of CJ, EG, AHK, ALN, BDK, BFN, DFP, HLP and KNP. As these possible effects are indistinguishable with the design used, they are referred to as aliased. The highest probability is that a single one of these accounted for the observed effect, and that it was a 2FI, as 3FIs are rarer and typically smaller in magnitude. Additionally, none of the possible 3FIs contained the terms that showed as main effects (G, E, J or C), whereas genuine interactions usually come alongside some of their lower order hierarchy. Given the magnitude of both G and E in the analysis, it was considered highly likely that the large positive interaction was EG, as it is assigned in FIG. 5. It was concluded that it was likely that the reason for the large number of zeros was that a conjunction of the correct strain and enough time was needed to get enzyme production. Therefore, to obtain more data on the system, an iteration was run where the correct strain was specified, and increased time was given for production. Hence, at the conclusion of the multi-factorial screen one process factor and one genetic factor had unexpectedly been identified as having an important influence on the performance of the overall process.

Iteration

Figure 6:
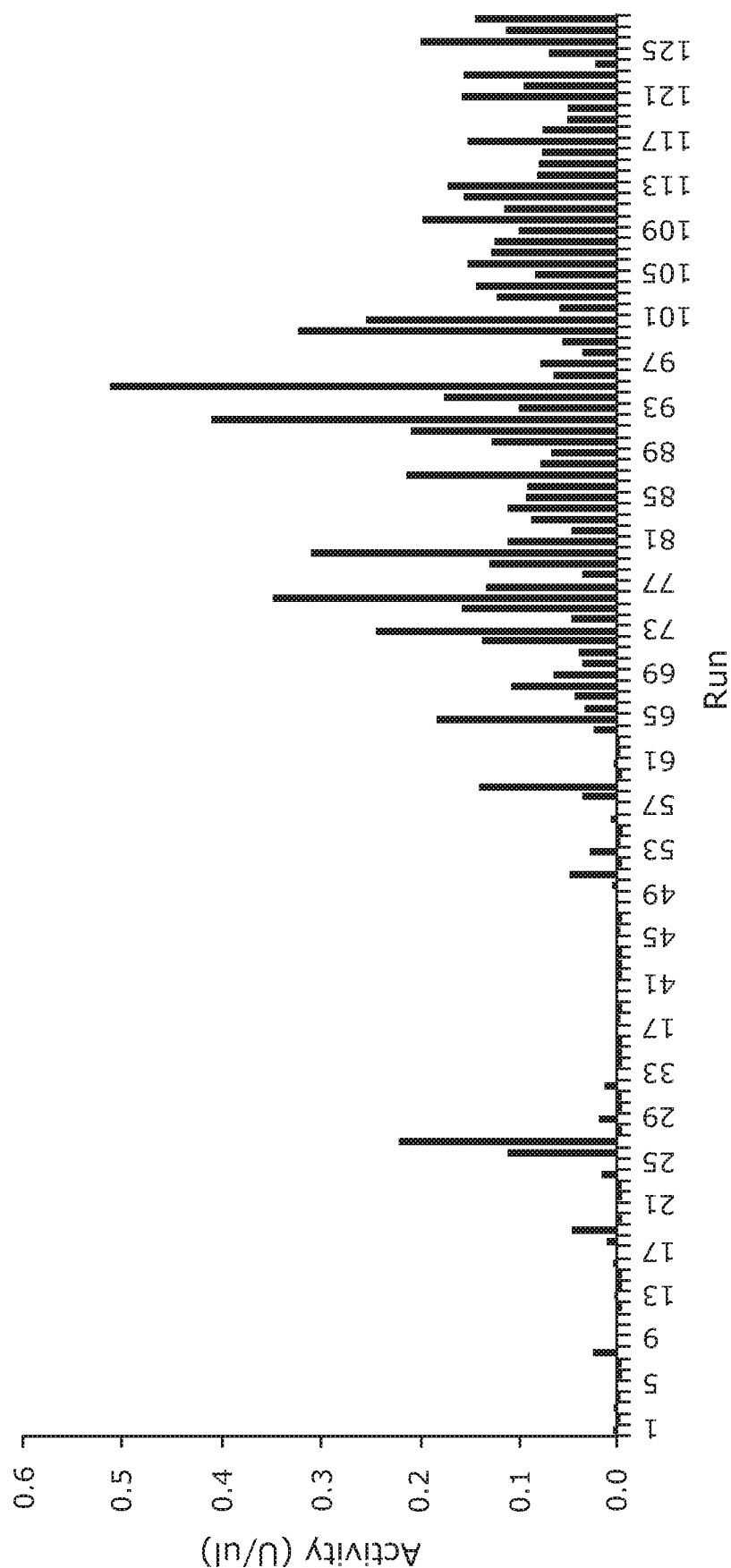
FIG. 6 is a graph of enzymatic activity observed per microliter of unpurified E. coli lysate following an iteration step according to one embodiment of the present invention. Runs 1-64 correspond to the data shown in FIG. 4.
Figure 7:
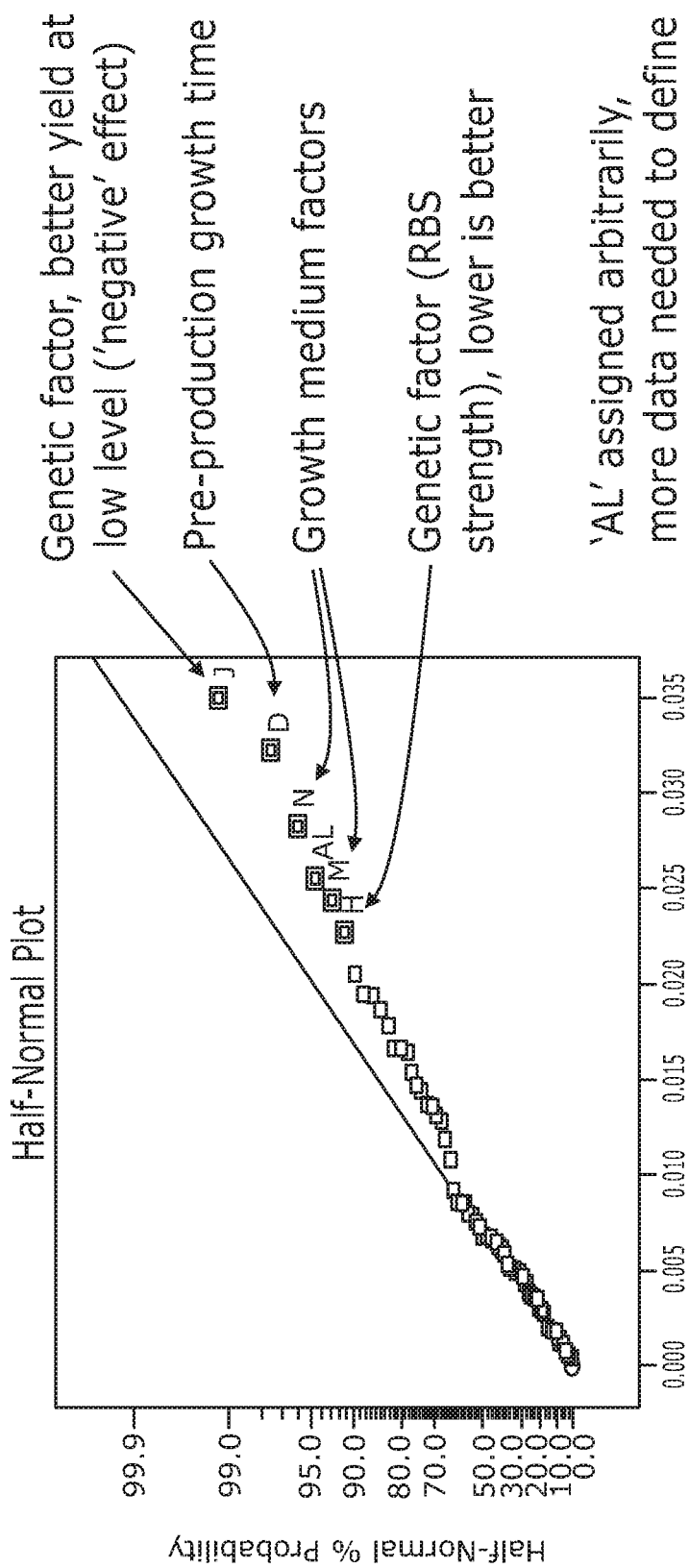
FIG. 7 is a half normal plot of the results obtained in the iteration step.

The shifted design space used for the iteration gave the results as shown in FIG. 6 (the initial factor screen results—runs 1-64—are also shown for comparison). With the design now focussed in a more productive area of design space, many more previously unrecognised factors now became evident as important to the process (FIG. 7). We focussed on the effects of greatest magnitude: most were main effects (single factors), including genetic factors (H and J), medium composition factors (M and N) and a different timing factor to the one observed in the factor screen. The primary factors observed in the factor screen (E and G) were no longer observed as effects, indicating that they were having no further effect at the ranges they were now investigated over.

Refinement

The main difference between this step and the factor prioritisation steps that preceded it is the significantly reduced number of factors addressed. The results from the previous experiments were used to determine which factors were having least effect on the system. These factors were fixed at a single level for future experimentation. Since the effect of these factors has been shown to be minimal the levels can be set at whatever may be cheapest or most convenient, whilst still being within the previously investigated space. In the refinement phase, factors A-C, G, L and N-P were fixed, and factors D-F, H-K and M were selected for deeper investigation (reassigned as D-F, A-C and G, respectively).

Figure 8:
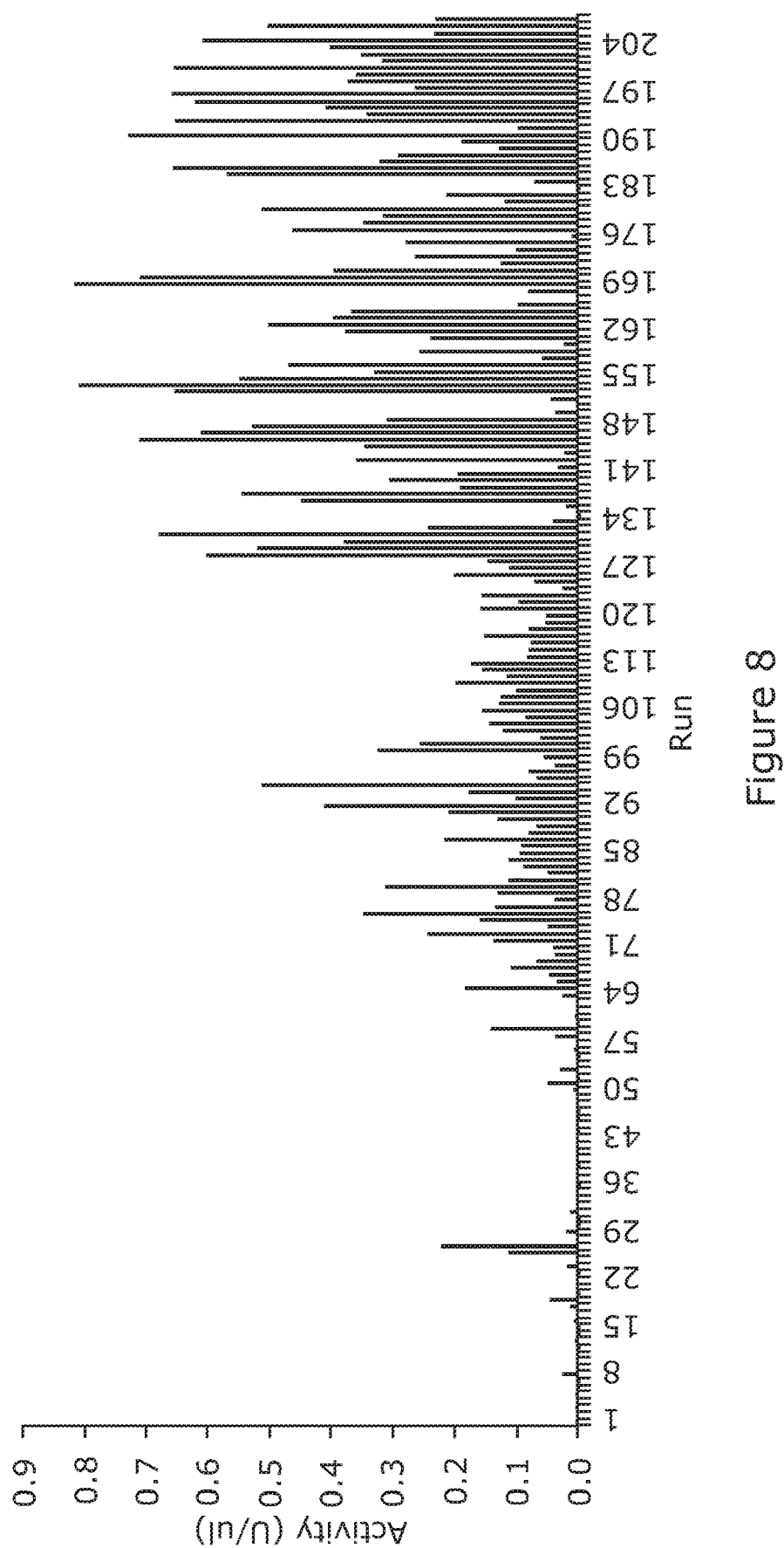
FIG. 8 is a graph of enzymatic activity observed per microliter of unpurified E. coli lysate following a refinement step according to one embodiment of the present invention. The results of previous runs shown in FIGS. 4 and 6 are also shown for comparison.

Another major difference from the previous steps is that the design space was moved again to a region predicted by the iteration step to be more productive, so that the refinement was continued as more information about the system was obtained. Results for the refinement, alongside those for previous steps are shown in FIG. 8. Replicated centre points were also included as a direct measure of noise. Four points are needed for a good estimate, additionally they should be replicated fourfold to account for categoric factors, leading to 16 additional runs in this round of experimentation.

Figure 9:
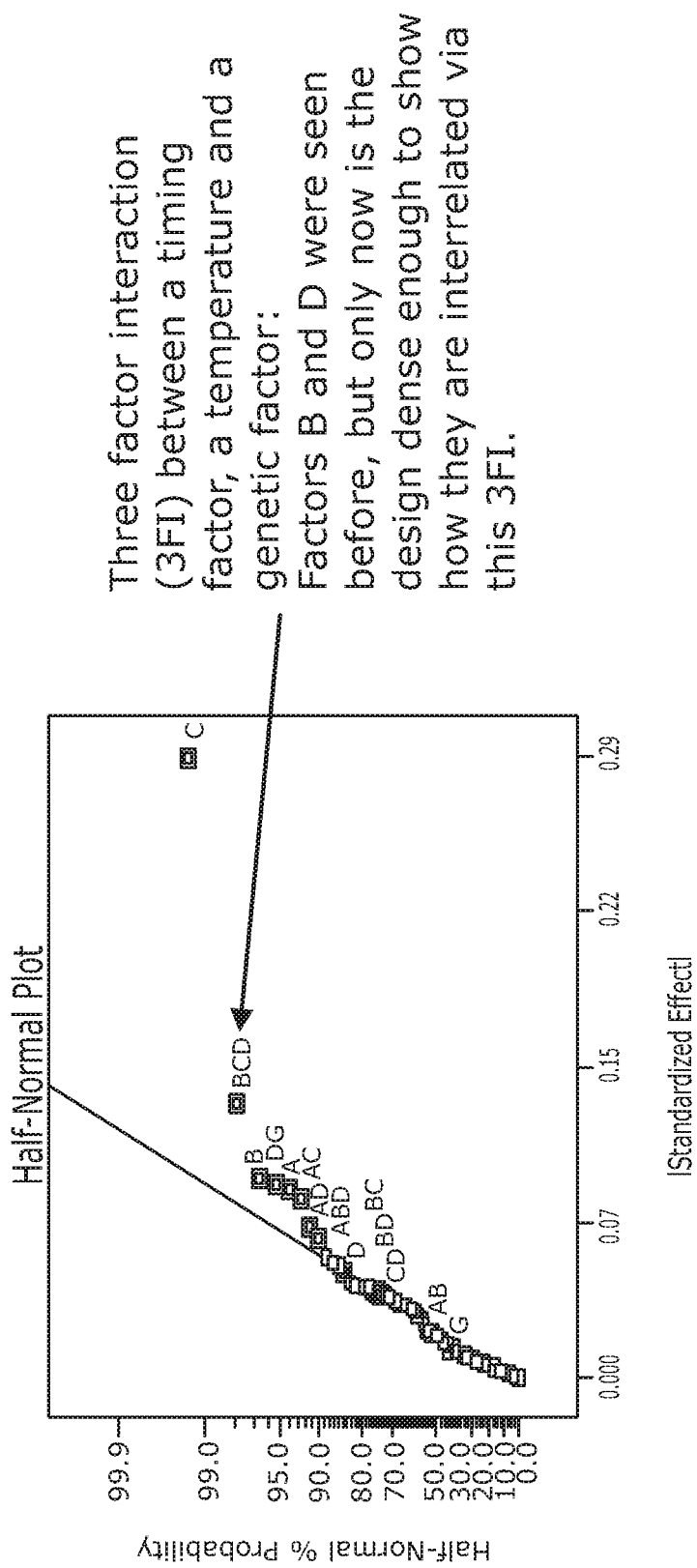
FIG. 9 is a half normal plot of the results obtained in the refinement step.
Figure 10:
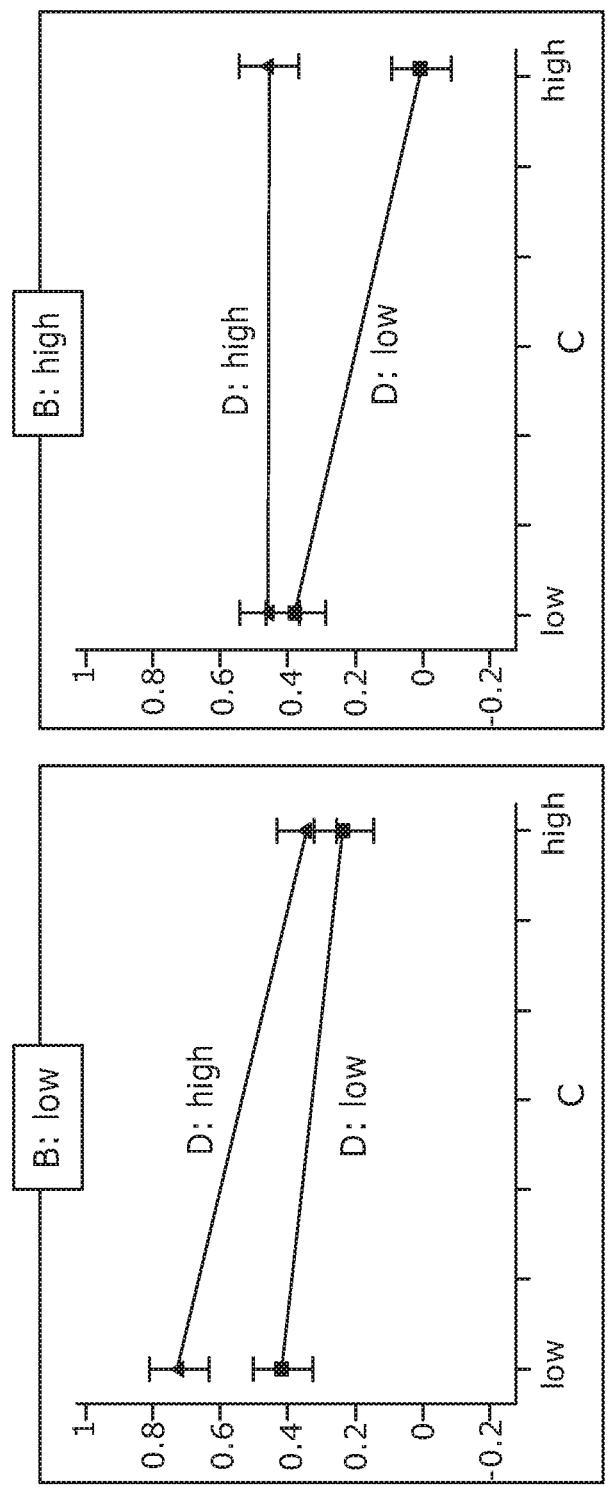
FIG. 10 shows model graphs showing the nature of the three factor interaction identified in FIG. 9.

FIG. 9 shows the analysis of the data obtained from the refinement. Owing to the much denser design at this stage ($2^{7-1}$), the BCD interaction observed did not have any aliases, assuming that there were no 4FIs. The implications of this 3FI were that three apparently unrelated factors—a genetic factor (B), a process temperature (C) and a timing factor (D)—were interacting in such a way that a combination of the correct levels were required to get the highest yields, see FIG. 10. Owing to the lack of other factors observed as significant at this point, it was possible to eliminate more factors from further investigation and progress to the optimisation step.

Optimisation and Robustness

Figure 11:
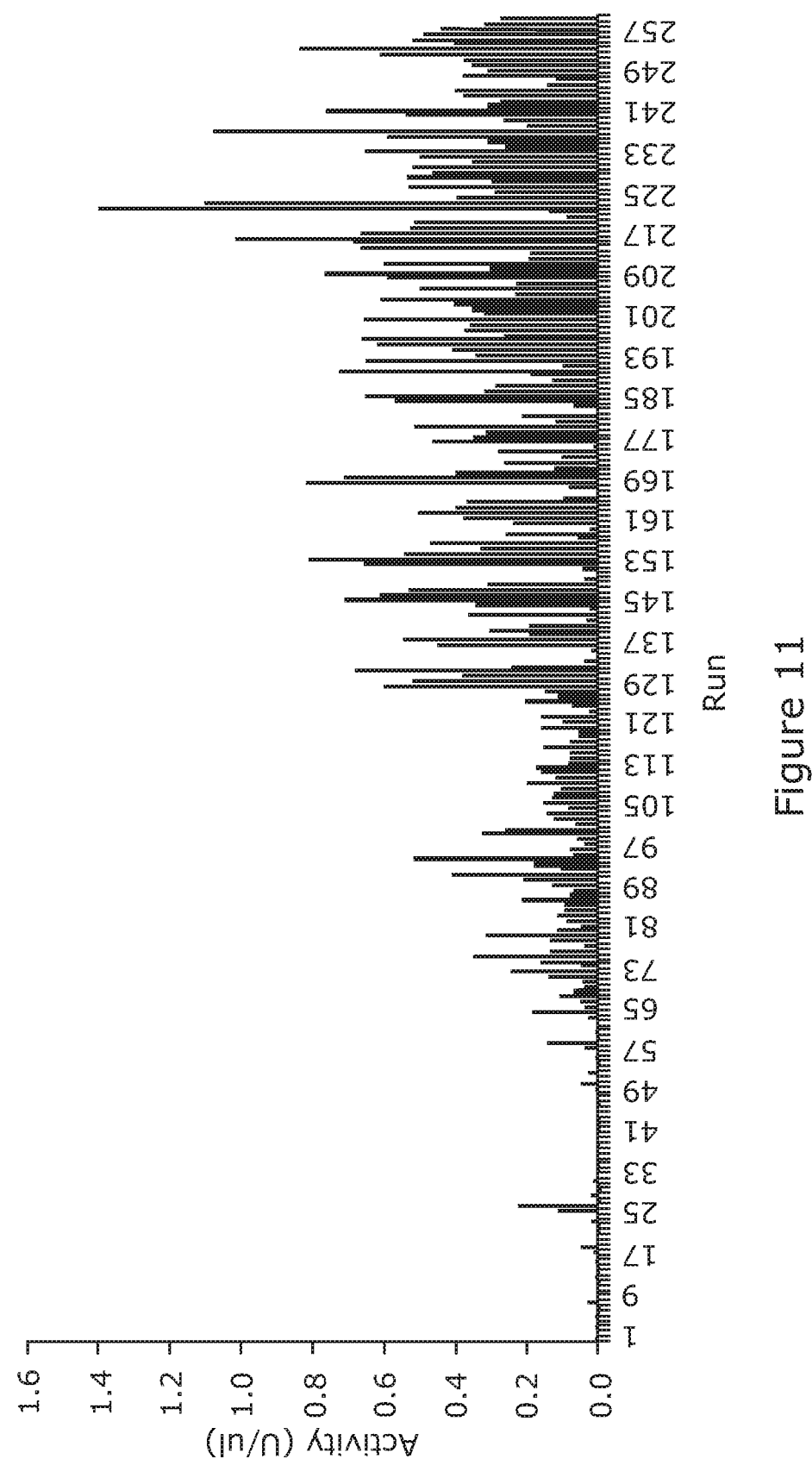
FIG. 11 is a graph of enzymatic activity observed per microliter of unpurified E. coli lysate following an optimisation step according to one embodiment of the present invention. The results of previous runs shown in FIGS. 4, 6 and 8 are also shown for comparison.

At this stage a central composite design was run, which consists of a full factorial (24), augmented with additional extreme points {+α, −α} and centre points, which allows 2nd order polynomials to be fitted. This design led to still further significant gains in productivity, as shown in FIG. 11, and indicated a specific area of greatest productivity. The predicted optimum was then tested, with runs around that area of design space, to ensure that the conditions identified gave consistently good yields.

Figure 12:
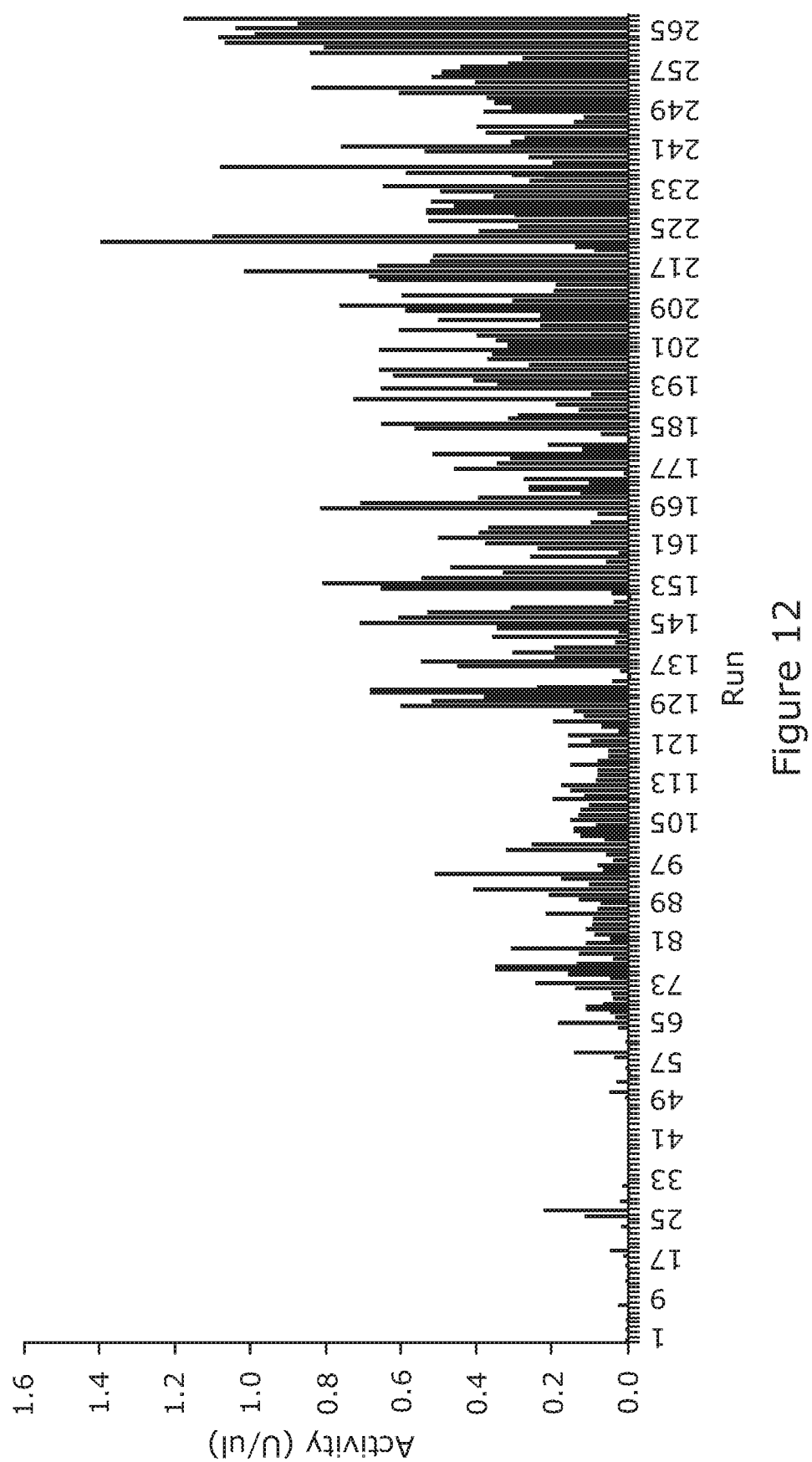
FIG. 12 is a graph of enzymatic activity observed per microliter of unpurified E. coli lysate showing the results of all previous runs shown in as well as the final optimisation steps.

The robustness of the present study showed that it was feasible to achieve a specific activity of consistently greater than 0.8 U/μl for the product enzyme, human carboxylesterase 1 (see FIG. 12). Overall, the best results were >200× better than any known literature precedent for this enzyme, and 7× better than the best estimation of industry yields based on analysis of a comparable product given that this product is sold as crude *E. coli* lysate whose specific activity is seven-fold lower than that obtained according to the method of the invention.

Example 2—Automation of Multifactorial Experiments

As the number of factors increases, the complexity of the experiments required increases substantially. This precludes effective manual execution, but it is possible to automate key steps, and ultimately whole experiments to render higher factor level experimentation tractable. Here we describe DEXML: software that facilitates automated execution of liquid handling steps involved in a multifactorial experiment. The example here is directed to medium preparation, but the skilled person will appreciate that this framework can equally be applied to other processes including the complex genetic construct assembly required to investigate high numbers of genetic factors.

DEXML produces instructions for liquid-handling robots and setup instructions for users of such robots in order to implement liquid-handling stages relevant to designed experiments. Given a set of parameters defining composition of liquid media or bacterial cultures the system calculates required volumes and concentrations of stock components, requirements for liquid handling resources such as tips, defines a setup plan for deck layout and produces an instruction script for direct execution by the robot.

Inputs: DesignExpert text file, Configuration file (CSV format)
Outputs: Liquid handling instructions
Parameters: Set in configuration file
Dependencies: Labware definitions.
Implementation: Ruby 1.9.3 scripts
Technical Details DEXML is a command-line tool for creating implementations of designed experiments. The best way to understand its operation is through a description of use. The workflow is as follows:

First, the user creates their experimental design using DesignExpert™ Factors directly implemented by the robot (concentrations or volumes) must be specified as actual levels rather than in coded form. The design must be exported in DesignExpert™ text format.

Second, the user creates a configuration file for the software. This file is in a simple proprietary format which allows the user to define a series of experimental stages which the robot will execute. An example configuration file is set out below:

```
~~~~~~~~~~~~~~~~~~~~~~~~~~~~~~~~~~~~~~~~~~~~~~~
Implementation for Culture Media Prep
~~~~~~~~~~~~~~~~~~~~~~~~~~~~~~~~~~~~~~~~~~~~~~~
stage, med_prep_c,
Components
[c9],F,watersolution,
[c8],F,watersolution,
[c7],F,watersolution,
[c6],F,watersolution,
[c5],F,watersolution,
[c4],F,watersolution,
c3,F,watersolution,
[c2],F,watersolution,
c1,F,watersolution,
T3,F,temperature,
CultureV,F,totalvolume
buffer,V,watersolution
kanamycin,10,watersolution,
Inducer,10,dummyliquid
InocV2_V,F,dummyliquid
groups,,
,,
,,
parameters,,
c9-stock,100,
c8-stock,100,
c7-stock,100,
c6-stock,100,
c5-stock,100,
c4-stock,100,
c2-stock,100,
volume_multiplier,1
volumeunit, 1000000,       # specifies microlitres ([stock] in g/L).
platefile,plates/plateOne96well2mlconicalbottom.txt,
sourceplatefile,plates/plateOne96well2mlconicalbottom.txt,
robotfile,robots/felixForBigExperiment.rbt,
platedir,plates/,
tipdir,plates/,
grouping,simple,        #col-wise std order.
test_execution,1,       #automated check run.
pipette_to_liquid,1,
```

An experimental stage is essentially a set of designed experimental runs laid out in an appropriate liquid handling receptacle such as a 96-well plate. Thus in an experiment with factors pertaining to different stages a separate implementation for each stage can be produced which only considers the factors that are relevant for that stage.

Each stage entry in the config consists of declarations that a particular component is needed when implementing that stage. Liquid components can be fixed or variable, the variability either being determined based on the experimental design or on the desired target volume of each experiment. Non-liquid components can also be specified if they place constraints on the design layout (a good example of this is when plates must be incubated at different temperatures). Each component is given a designation according to whether it is a liquid (and if so what type of liquid) or some other experimental variable such as time, temperature or shaking speed. Finally where factors are separate in the design file but come in as groups (typically genetic factors) the config file provides the ability to define how these factors are grouped together. Finally the config contains information on the concentrations of relevant stock solutions and optional commands for the implementer.

The software is then run on the config file and Design-Expert™ file to produce an implementation of each stage defined in the config. The program works as follows: first it loads the two files and extracts the required information. Subsequently for each stage it determines how each experiment should be implemented in terms of the required liquid components and what volumes of these are needed. Concentrations are converted into volumes using the configuration information such as stock solution concentrations, adjusting these concentrations as necessary to ensure that parameters of the liquid handler (e.g. minimum transfer volume) are satisfied.

Next the layout of the experiments on the output plates is defined. This can be set by the user via judicious choice of factor assignments but can also be modified through the choice of several automated options in the config file. Given the plate layout, the software then determines how much of each stock component is required and defines how they should be laid out on the robot deck given constraints on labware positions and types.

Once a layout has been defined the system defines an execution plan to enact the required transfer of liquids and implement the experiments. This consists of a set of robot instructions for loading/unloading tips, aspirating and dispensing volumes of particular liquids at required positions and other peripheral features such as changes in liquid handling adaptor. The plan is devised on a per-component basis, with the full plan being assembled by concatenating the subplans for all components. Each component subplan has two stages: first the system attempts to use any bulk-handling facility to pipette volumes to and from several wells simultaneously (at present this is restricted to 8-channel column-by-column pipetting). Then any remaining required volume is made up using individual transfers. Operations are planned in order to ensure that transfer volume limits (upper and lower) are not transgressed at any stage.

The basic plan is then passed to an optimizer layer which refines the execution to improve speed via operations such as determining where the channel can be used to pipette from one source to multiple destinations (multipipetting) without risk of contamination, or to improve volumetric accuracy.

The instructions are then passed to a simulator layer which checks that component volumes, liquid handling channel limitations and tip resources are not exceeded during execution and that the composition of the final output plates is as required.

If the plan is validated it is output in an appropriate machine-readable format for implementation on the liquid-handling platform. A set of human-readable instructions is also produced for manual validation, if required. Robot setup instructions detailing component layout on source plates are also produced in a simple text format for viewing with appropriate software.

Unless otherwise indicated, the practice of the present invention employs conventional techniques of chemistry, molecular biology, microbiology, recombinant DNA technology, and chemical methods, which are within the capabilities of a person of ordinary skill in the art. Such techniques are also explained in the literature, for example, M. R. Green, J. Sambrook, 2012, Molecular Cloning: A Laboratory Manual, Fourth Edition, Books 1-3, Cold Spring Harbor Laboratory Press, Cold Spring Harbor, N.Y.; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

What is claimed is:

1. A system for increasing process performance in a biological process, wherein a biological process is a specific sequence of transformative events performed upon a starting material in order to achieve a specified purpose or goal, wherein the process uses complete living cells or any of their components, wherein the process results in the transformation of the starting material into a product, the system comprising:
(i) a processor adapted to implement a method comprising:
(a) an identification phase, in which at least seven factors are identified, wherein a factor is defined as a feature of or within a process that when modified will affect the performance of the process, and wherein the factors are selected from at least two process factors and at least two genetic factors, wherein process factors are selected from a group comprising of features of the equipment, environment, protocol, reagents, handling of cells and process design; and wherein genetic factors are selected from qualitative and quantitative features associated with any genetic material involved in the process;
(b) a factor screening phase, in which individual and combined contributions to process performance of each of the at least seven factors as described in (a) are determined, such that the presence of multifactorial interactions might be identified, wherein factors are deemed to interact when the effects of changes to one factor are dependent on the value of another factor; and
(c) a refinement phase, in which interactions that result in an increase in process performance between the at least seven factors are identified and tested; and
(ii) a laboratory automation apparatus, wherein the apparatus is controlled by the processor and is configured so as to implement the factor screening and refinement phases.

2. The system of claim 1, wherein the laboratory automation apparatus is further configured so as to implement an optimization phase, in which higher order interactions are used to generate a higher-order model based upon a limited number of factors identified as contributing most significantly to an increase in process performance.

3. The system of claim 1, wherein the laboratory automation apparatus comprises one or more of the group consisting of: liquid handling and dispensing apparatus; container handling apparatus; a laboratory robot; an incubator; plate handling apparatus; a spectrophotometer; chromatography apparatus; a mass spectrometer; thermal-cycling apparatus; and centrifuge apparatus.

4. The system of claim 1, wherein the processor implements the method of claim 1 as part of a laboratory information management system (LIMS).

5. The system of claim 1, wherein the biological process comprises a plurality of process steps, wherein process steps are sub-steps of a process that are each applied in sequence on inputs including at least one physical input in order to produce an output including at least a physical output such as a product, and optional additional data outputs.

6. The system of claim 1, wherein the at least one process step comprises a manufacturing process.

7. The system of claim 1, wherein the at least one process step comprises an analytical process.

8. The system of claim 1, wherein each factor is modified over at least two levels, wherein a level corresponds to a parameter range or characteristic associated with the factor.

9. The system of claim 1, wherein the multi-factorial interaction comprises at least one two-factor interaction.

10. The system of claim 1, wherein the multi-factorial interaction comprises at least one three-factor interaction.

11. The system of claim 1, wherein the multi-factorial interaction comprises at least one interaction that comprises more than three factors.

12. The system of claim 1, wherein the multi-factorial interaction comprises at least one process factor and at least one genetic factor.

13. The system of claim 1, wherein the at least one process factor is selected from the group consisting of: temperature; pH; titrants; buffer concentration; reagent concentration; growth media composition; nutrient concentration; waste-product concentration; oxygen concentration; reactor volume; fermentation volume; impeller speed; seed culture conditions; air flow; pressure; feed composition; feed rate; feed timing; antifoam type; antifoam concentration; shaking speed; presence of baffles; size of baffles; position of baffles; bioreactor geometry; inducer concentration; induction time; stock culture generation method; stock culture storage conditions; and timings of any process step.

14. The system of claim 1, wherein the at least one genetic factor is selected from the group consisting of: vector type; genetic background; epigenetic modifications; gene variant; gene identity; host organism species; host organism strain; promoter type; codon usage; ribosome binging site; origin of replication; selection marker; site of chromosomal integration; leader sequence; fusion protein; fusion tag; siting of fusion element at N or C terminus; operator usage; activator usage; operon design; mRNA 5' optimization strategy; copy number; orientation of genetic constructs; insulator elements; siRNA candidates; non-coding nucleic acid; gene knockouts; and gene upregulation.

* * * * *